United States Patent [19]

Samson et al.

[11] Patent Number: 5,252,387
[45] Date of Patent: Oct. 12, 1993

[54] FABRICS WITH INSECT REPELLENT AND A BARRIER

[75] Inventors: Richard D. Samson; James M. McKinney, both of North Augusta; John Russell, Aiken, all of S.C.

[73] Assignee: Graniteville Company, Graniteville, S.C.

[21] Appl. No.: 11,807

[22] Filed: Feb. 1, 1993

Related U.S. Application Data

[63] Continuation-in-part of Ser. No. 678,061, Apr. 1, 1991, Pat. No. 5,198,287.

[51] Int. Cl.$^5$ .................. A01N 25/34; B32B 33/00; E04H 15/54
[52] U.S. Cl. ..................................... 428/248; 8/115.7; 8/182; 8/115.59; 135/115; 424/403; 428/252; 428/264; 428/265; 428/907
[58] Field of Search .................. 8/115.7, 182, 115.59; 135/115; 424/403; 428/248, 252, 264, 265, 907

[56] References Cited

U.S. PATENT DOCUMENTS

| | | | |
|---|---|---|---|
| 3,769,060 | 10/1973 | Ida et al. | 428/907 |
| 3,859,121 | 1/1975 | Yeadon | 428/907 |
| 3,995,034 | 11/1976 | Strobel | 514/159 |
| 4,594,286 | 6/1986 | McKinney | 428/252 |
| 4,765,982 | 8/1988 | Ronning et al. | 424/402 |
| 4,833,006 | 5/1989 | McKinney et al. | 428/257 |
| 5,089,298 | 2/1992 | McNally et al. | 427/322 |

*Primary Examiner*—James C. Cannon
*Attorney, Agent, or Firm*—Clifton Ted Hunt

[57] ABSTRACT

An insect repellent fabric has a coating containing permethrin and a plasticizer, and a barrier covers the coating to protect the permethrin from degradation by ultraviolet light and oxygen. The barrier may be an acrylic coating or film, aluminum foil, a urethane coating or film, or an outer fabric barrier such as an awning or a tent fly.

9 Claims, 2 Drawing Sheets

FABRICS WITH INSECT REPELLENT AND A BARRIER

CROSS REFERENCE TO RELATED APPLICATIONS

This application is a continuation-in-part of our application Ser. No 678,061, filed Apr. 1, 1991 for INSECT REPELLENT TENT FABRIC, now U.S. Pat. No. 5,198,287.

FIELD OF THE INVENTION

This invention relates to coated fabrics that are treated to be flame retardant, water resistant, and insect repellent. According to the invention, the duration of insect repellence is increased by the use of one or more barriers to protect the treated fabric from exposure to ultra violet light.

BACKGROUND OF THE INVENTION

It has been demonstrated in our earlier patent application, Ser. No. 678,061, that permethrin incorporated into a fire retardant and water resistant coating on the inside of a tent provides protection against insects for as long as six months. The plasticizer in the coating provides the permethrin mobility to the coated fabric surface in a controlled release manner.

Since permethrin is prone to decomposition into an inactive non-insecticidal product in the presence of oxygen and ultraviolet light, it is important to minimize migration of the permethrin to the exterior surface of the tent or other fabric. The fabric substrate, itself, is recognized in our application Ser. No. 678,061 as functioning as a barrier to the migration of the permethrin from the coating on the inside of the fabric to the outside of the fabric, where it is exposed to oxygen and ultraviolet light.

As explained in our earlier application, Ser. No. 678,061, permethrin is a synthetic pyrethroid which exhibits repellent as well as knockdown and kill activity against insects. Pyrethroids, including both the naturally occurring compounds and their synthetically prepared analogs effectively control a variety of pests, such as houseflies, mosquitoes, cockroaches, etc.

They are not harmful to plants, food, animals and humans, and leave no harmful residues. Permethrin is environmentally safe and has been found to be compatible with coating compositions containing water repellent chemicals and flame retardant chemicals, used for tent fabric, without adversely affecting the desired properties of the coated fabric.

Despite these highly favorable characteristics, permethrin has had only limited general utility because of its relatively short-lived insecticidal activity. This is due to its decomposition into an inactive, non-insecticidal product in the presence of oxygen and ultraviolet light. The speed of this decomposition is dependent upon the environment in which the permethrin is placed, but typically takes place in from several hours to several days or weeks. The instability of permethrin severely limits its usefulness as an insecticide.

Prior attempts to stabilize pyrethroids against degradation have included encapsulation and the addition of antioxidants and photostable ultraviolet light absorbent compounds to solutions of pyrethroids. Encapsulation has not been effective because the pyrethroids degrade almost as quickly inside the capsules as they do unencapsulated. Only moderate success in reducing degradation has been obtained by the addition of antioxidants and photostable ultraviolet light absorbent compounds to solutions of pyrethroids. Their moderate success is largely off-set by unsightly residues which are hard to remove.

Various techniques have been suggested for providing sustained release of a pyrethroid as an insect control agent. For example, U.S. Pat. No. 4,056,610 to Barber discloses a microcapsule insecticide composition in which a pyrethroid permeates a porous shell wall and maintains an effective level of the pyrethroid upon the outer surface of the shell wall to control insects for up to four days (then considered an extended length of time within the art). Control is achieved by killing insects which contact the pyrethroid released through the capsule wall.

U.S. Pat. No. 4,765,982 to Ronning discloses an insect control device comprising a plurality of rough surfaced cellulosic fibers wherein there is self-adhered to the surface of the fibers a liquid insecticide composition microencapsulated in a capsule whose shell is permeable to the liquid insecticide. The micro-encapsulated insect control agents disclosed in U.S. Pat. No. 4,956,610 to Barber are named as the preferred insecticide for use in Ronning's invention.

Ronning's insecticide-treated-rough-surfaced cellulosic fibers are formed into webs, tapes, sheets, pads, and various other relatively flat shapes suitable for use in particular locations, such as a ribbon-like tape for placement along the base of a building or door.

Ronning teaches that smooth-surfaced fibers do not act as good sites for adhesion of microencapsulated insect control agents. Ronning's rough surfaced cellulosic fibers treated with an insecticide are not suitable for a tent fabric. The texture of the rough surfaced fibers is not satisfactory and they are neither water repellent or flame retardant.

SUMMARY OF THE INVENTION

It is the primary object of this invention to prolong the insect repellent properties of fabrics treated with permthrin and a mobilizing agent by the use of barriers to the migration of plasticizer mobilized permethrin to exterior surfaces. Examples of satisfactory barriers are polymeric coatings, films, foils, fabrics, and surface treatments which are resistant to plasticizer migration.

In addition to tents, the end use of fabrics treated in accordance with the invention include uses which are not treated to be fire retardant or water repellent, such as ankle wraps and outerwear. A barrier material, such as aluminum foil, may be used on the inside of the fabric to prevent skin contact with the permethrin.

DETAILED DESCRIPTION OF THE INVENTION

The fabrics of this invention are coated on one surface with permethrin and a suitable plasticizer, such as dioctyl phthalate or zirconium wax, and tent fabrics are also coated with suitable chemicals to render the fabric water repellent and flame retardant. The permethrin is applied to the coating on the inside of a tent fabric, or substrate, as described in parent application Ser. No. 678,061. The disclosure of said parent application is incorporated herein by reference.

Insect Repellent Coating for Tent Fabric

An example of a coated tent fabric that is suitable for use with the present invention is one whose inner surface has been treated with the following insect repellent coating:

| COMPONENT | PERCENTAGE | FUNCTION |
|---|---|---|
| Emkay B.C. | 0.45 | Defoamer |
| Polyvinyl Chloride Polymer (Geon 576) | 18.37 | Binder |
| Dioctyl Phthalate | 5.99 | Plasticizer |
| Sodium Salt of Phosphated Ester | 0.25 | Surfactant |
| Antimony Trioxide | 13.83 | Flame Retardant |
| Kaolin (Hydrated Aluminum Silicate) | 19.20 | Flame Retardant |
| Methylated Melamine Formaldehyde Resin | 1.72 | Cross-linker |
| Methylcellulose | 0.27 | Thickener |
| Bromochlorinated Hydrocarbon | 27.66 | Flame Retardant |
| Zirconium Wax Complex | 1.51 | Water Repellent |
| Pigment Systems | 1.79 | Color |
| Acrylic Copolymer (Acrysol ASE-60) | 0.98 | Thickener |
| Metasol TK-100 Powder | 0.15 | Mildew Inhibitor |
| Permethrin | 07.83 | Pesticide |
| | 100.00% | |

Permethrin is an immobile material but can be made mobile with a plasticizer. In addition to serving as a water repellent in the normal coating for tent fabric, the zirconium wax complex also serves as a plasticizer and as a protector against oxygen for the permethrin. The wax creates a shell around the permethrin that protects the permethrin from degradation by oxygen after the permethrin reaches the surface of the coating. The wax and plasticizer also mobilize the permethrin to the extent of keeping enough permethrin on the surface of the coating to be an effective insect repellent for a much longer period of time than has heretofore been possible.

The Added Advantage of A Barrier

It has been discovered that the efficacy of the insect repellency is significantly increased by using one or more barriers on or over the outer surface of a permethrin treated fabric to provide additional protection of the treated fabric by preventing or minimizing the exposure of the permethrin to oxygen and ultraviolet light. Suitable barriers can be formed of polymeric coatings, films, foils, fabrics, or surface treatments which are resistant to plasticizer migration.

Figure 1:
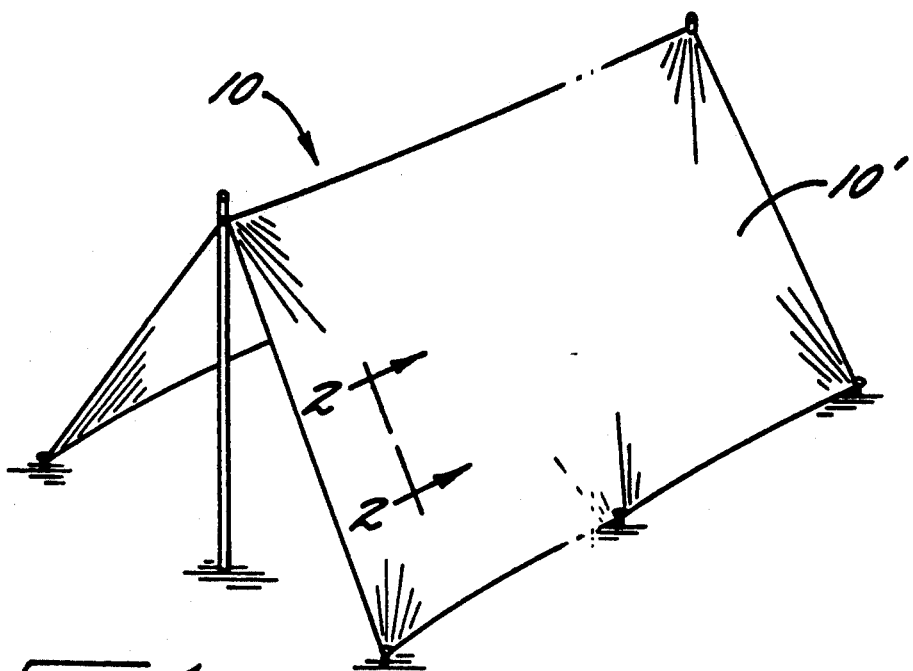
FIG. 1 is a perspective view of a tent which has been treated with an insect repellent and barrier in accordance with the invention.
Figure 2:
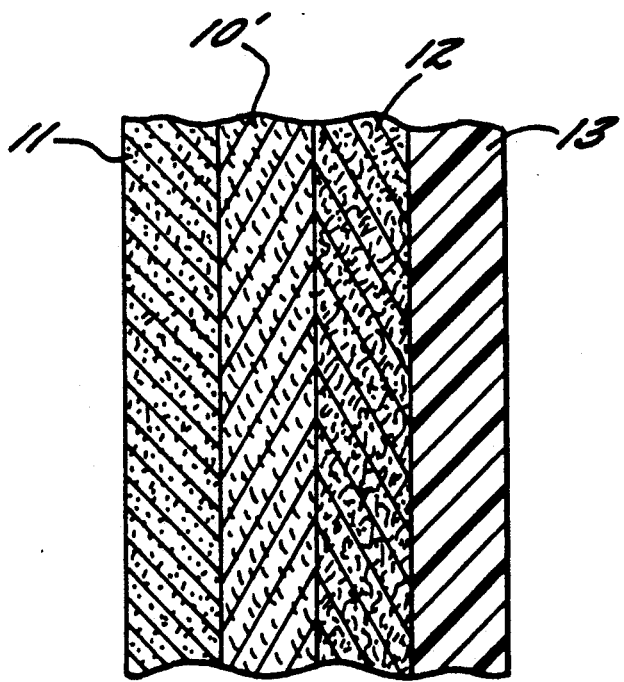
FIG. 2 is a sectional view taken substantially along the line 2—2 in FIG. 1.

FIGS. 1 and 2 illustrate a tent fabric 10 that has been treated with the foregoing insect repellent coating 11 on the inner surface of the fabric and with a water repellent and fire retardant coating 12 on the outer surface of the fabric. A barrier of acrylic coating 13 overlies the coating 12 on the outer surface of the fabric 10.

Figure 3:
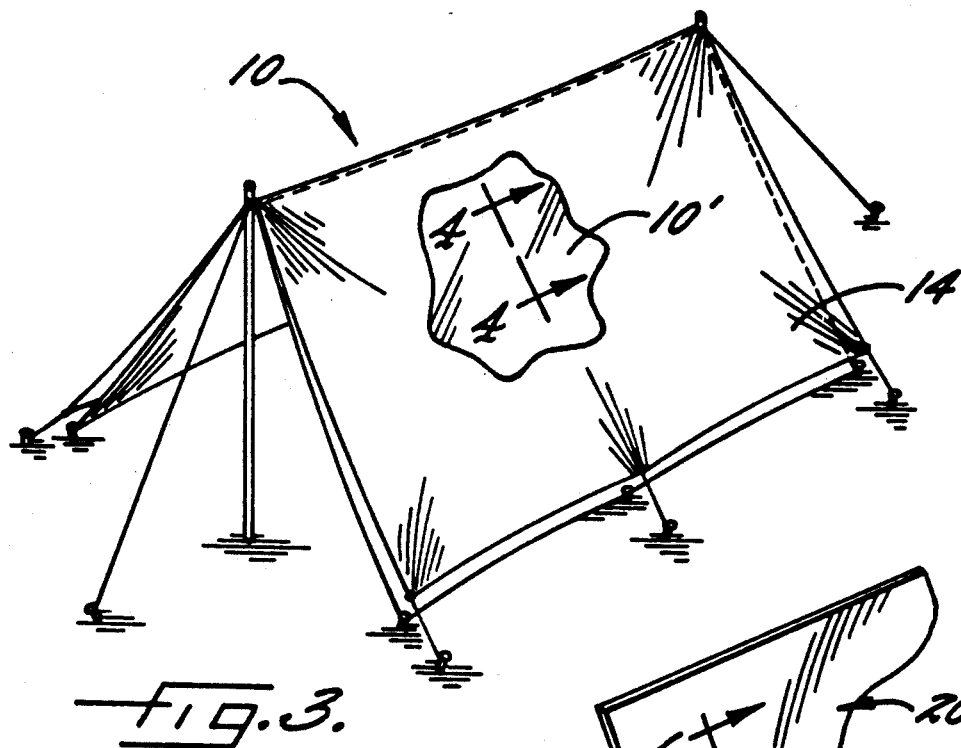
FIG. 3 is a perspective view of a tent, with parts broken away, which has been treated with an insect repellent and showing a modified form of barrier in accordance with the invention.
Figure 4:
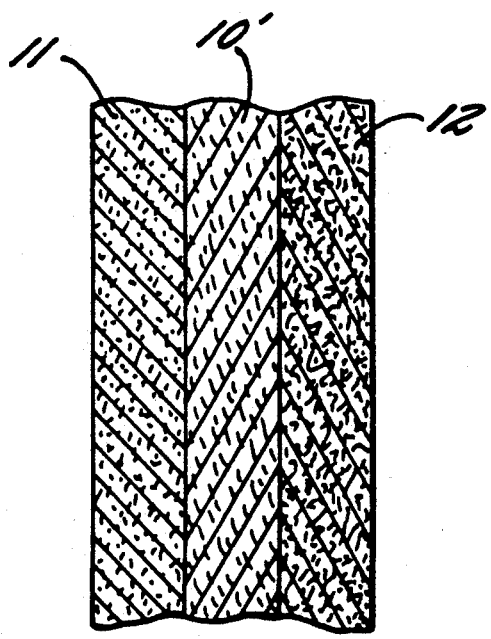
FIG. 4 is a sectional view taken substantially along the line 4—4 in FIG. 3.

FIGS. 3 and 4 illustrate the tent fabric 10 treated with the same coatings 11 and 12 as illustrated and described in connection with FIGS. 1 and 2, but the film barrier 13 has been omitted from the outer coating 12. Instead a conventional tent fly 14 is spaced above the tent 10 to serve as a barrier against ultraviolet radiation onto the tent 10 and thereby prevent degradation of the permethrin by ultraviolet light. The tent fly 14 may be preferred to acrylic coating or aluminum foil as a barrier in hot climates because of the additional insulation provided by the air space between the tent 10 and the tent fly 14.

Figure 5:
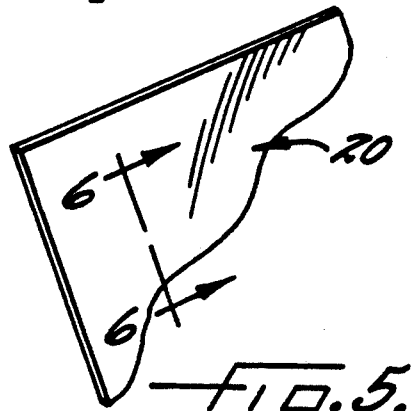
FIG. 5 is a fragmentary perspective view of a piece of fabric which has been treated with an insect repellent.
Figure 6:
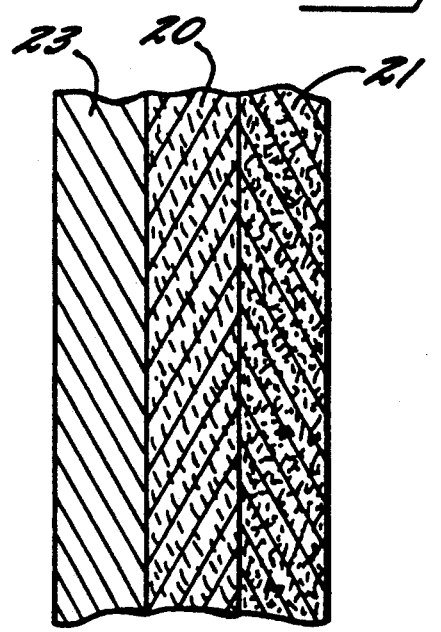
FIG. 6 is a sectional view taken substantially along the line 6—6 in FIG. 5.

FIGS. 5 and 6 illustrate a permethrin coating applied to a fabric used for another purpose, such as ankle wraps and outerwear. Here, the permethrin coating comprises simply the insect repellent permethrin and a suitable plasticizer for mobility of the permethrin within a polymeric binder.

In FIGS. 5 and 6, the fabric may be a suitable grade of cotton, a blend of synthetic and cotton or synthetic and wool, or wool, and is broadly indicated at 20. A permethrin coating 21 is applied to one surface of the fabric 20. A barrier of aluminum foil 23 to protect the skin is applied over the fabric 20 that will be closest to the wearer.

Testing

Various coatings and/or films, such as acrylic, urethane, and aluminum foil have been applied to the outer surface of permethrin treated samples of tent fabric for evaluation of their effectiveness as barriers to prevent the exposure of permethrin to the degrading effect of ultraviolet light and oxygen.

The Petri-dish Test

The efficacy of the barriers has been assessed by petridish testing. The petri-dish test employs disposable plastic petri-dishes measuring $60 \times 15$ millimeters inverted on $6.5 \times 7.5$ centimeter index cards to form a mosquito holding cell. A mosquito holding cell, with entrapped mosquitoes, was placed on one of the samples of permethrin and barrier treated tent fabric.

The Mechanics of The Test

Samples employed in the Petri-dish evaluation are identified below:

Test Series I

Five sample swatches of the tent fabric previously described were additionally treated with different barriers:

Sample 1 was treated with an acrylic coating barrier (Rohm & Haas AC33);
Sample 2 was provided with an aluminum foil barrier;
Sample 3 had no barrier coating or backing;
Sample 4 was treated with urethane/$TiO^2$ — Durance 11045-28W Raffi & Swanson;
All of the foregoing samples, 1 through 4, were weathered (weatherometer; no filter) for 500 hours.

Sample 5 is a control which had no barrier coating or film and no weathering.

All of the samples that were weathered were exposed in the weatherometer with the active permethrin treated side away from the weather.

Test Series II

Five tent fabric samples, numbered 10 through 14, were tested.

Samples 10 through 12 contained permethrin and were weathered for 100 hours;

Sample 10 was backed with flourex/polyethylene;

Sample 11 was backed with aluminum foil;

Sample 13 contained permethrin, but was not weathered;

Sample 14 did not contain permethrin and was not weathered.

The test results are set forth in the following table:

TABLE I

Mean knockdown of female *Aedes aegypti* exposed to tent fabric trated with permethrin or permethrin with acrylic or foil backing.

| Permethrin Fabric Code | Exposure Time | Hours Weathered | % KD 15 Min. | % KD 60 Min. | % KD 120 Min. |
|---|---|---|---|---|---|
| Series 1 A (average of 5 tests) | | | | | |
| 4 | 15 min. | 500 | 0 | 0 | NA |
| 3 | 15 min. | 500 | 0 | 0 | NA |
| 2 | 15 min. | 500 | 0 | 16 | NA |
| 1 | 15 min. | 500 | 0 | 0 | NA |
| 5 | 15 min. | 0 | 0 | 90 | NA |
| Series 1 B (average of 1 test) | | | | | |
| 4 | 30 min. | 500 | 0 | 0 | NA |
| 3 | 30 min. | 500 | 0 | 0 | NA |
| 2 | 30 min. | 500 | 0 | 80 | NA |
| 1 | 30 min. | 500 | 0 | 0 | NA |
| 5 | 30 min. | 0 | 60 | 100 | NA |
| Series II A (average of 2 tests) | | | | | |
| 10 | 15 min. | 100 | 0 | 50 | NA |
| 11 | 15 min. | 100 | 8.5 | 25 | NA |
| 12 | 15 min. | 100 | 0 | 20 | NA |
| 13 | 15 min. | 0 | 10 | 100 | NA |
| 14 (CK) | 15 min. | 0 | 0 | 0 | NA |
| Series II B (average of 2 tests) | | | | | |
| 10 | 120 min. | 100 | 0 | 80 | 100 |
| 11 | 120 min. | 100 | 0 | 70 | 100 |
| 12 | 120 min. | 100 | 0 | 30 | 100 |
| 13 | 120 min. | 0 | 0 | 90 | 100 |
| 14 (CK) | 120 min. | 0 | 0 | 0 | 0 |

For Series I, the data suggests that the availability of permethrin on the treated surface was insufficient to cause quick knockdown (within one hour) of mosquitoes in tests with exposure times of 15 and 30 minutes.

In Series II, a longer exposure time (120 minutes) increased the overall percentage of knockdown after 60 minutes. In Series IIB a 120 minute knockdown count was added to determine if an effect would be oberved with additional lapsed time.

Based on these results, it can be assumed that some additional knockdown may have occurred in Series I and II after 120 minutes.

It is apparent that weathered samples with barrier against mobilized permethrin migration to outside of fabric give significant gains in efficacy.

In accordance with the patent statutes, preferred modes of practicing the invention have been set forth. However, it will be apparent to those skilled in the art that many other modifications can be achieved without departing from the invention herein described and claimed.

We claim:

1. A coated tent fabric having a fabric substrate with a coated outer surface normally exposed to degrading elements of the atmosphere and a coated inner surface normally shielded by the fabric substrate from the degrading elements of the atmosphere, the coating on the outer and inner surfaces of said fabric substrate each containing a polymeric binder, flame retardant chemicals and water repellent chemicals and the coating on the inner surface of the fabric substrate containing permethrin as an insect repellent, wherein the improvement comprises a barrier over the coated outer surface of the fabric substrate, whereby the barrier protects the fabric substrate from ultraviolet light and oxygen and supplements the fabric substrate in protecting the permethrin from degradation.

2. A coated tent fabric according to claim 1 wherein the barrier is an acrylic coating or film.

3. A coated tent fabric according to claim 1 wherein the barrier is aluminum foil.

4. A coated tent fabric according to claim 1 wherein the barrier is urethane coating or film.

5. A coated tent fabric according to claim 1 wherein the barrier is a tent fly.

6. A fabric for wearing apparel, said fabric having a coating containing permethrin and a polymeric binder, wherein the improvement comprises a barrier covering a surface of the fabric intended to be disposed adjacent to the wearer's skin to protect the skin of the wearer of the fabric from permethrin migration.

7. A fabric according to claim 6 wherein the barrier is aluminum foil.

8. A fabric according to claim 6 wherein the barrier is an acrylic coating or film.

9. A fabric according to claim 6 wherein the barrier is a urethane coating or film.

* * * * *